United States Patent [19]

Brown et al.

[11] Patent Number: 4,713,471

[45] Date of Patent: Dec. 15, 1987

[54] METHOD FOR THE PREPARATION OF BENZYLOXYPHENOXY PENTANOATES

[75] Inventors: Richard W. Brown, Richmond; Richard D. Gless, Jr., Oakland, both of Calif.

[73] Assignee: Stauffer Chemical Company, Westport, Conn.

[21] Appl. No.: 896,794

[22] Filed: Aug. 15, 1986

[51] Int. Cl.$^4$ ............................................. C07C 69/76
[52] U.S. Cl. .................................. 560/53; 562/464; 562/463; 568/325
[58] Field of Search .................... 560/53; 562/464, 463

[56] References Cited

U.S. PATENT DOCUMENTS 4,540,804  9/1985  Wehrenberg ........................ 560/60
4,547,582  10/1985 Wehrenberg ........................ 580/60

Primary Examiner—Paul J. Killos
Attorney, Agent, or Firm—Paul R. Martin

[57] ABSTRACT

A method of producing benzoyloxyphenoxy pentanoic acid esters comprising the steps of: (a) reacting a compound of the formula

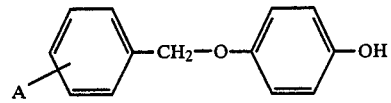

wherein A is as defined with a compound of the formula

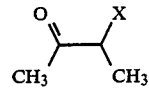

wherein X is as defined, in the presence of a base selected from carbonate salts of alkaline earth or alkali metals, a catalyst and a ketonic solvent to produce a 3-(4-benzyloxyphenoxy)-2-butanone; and (b) reacting said 3-(4-benzyloxyphenoxy)-2-butanone with a dialkyl carbonate of the formula (RO)$_2$CO, wherein R is an alkyl group having from 1 to 4 carbon atoms, in the presence of a suitable base and an organic solvent, to form alkyl 4-(4-benzyloxyphenoxy)-3-oxopentanoate.

10 Claims, No Drawings

METHOD FOR THE PREPARATION OF BENZYLOXYPHENOXY PENTANOATES

BACKGROUND OF THE INVENTION

The present invention relates to a method for the production of certain benzyloxyphenoxy pentanoates, compounds which are critical intermediates in the formation of certain aryloxyphenoxy pentanoates. Aryloxyphenoxy pentanoates are well known compounds which have been found to be particularly useful as post-emergent herbicides when used against various weed species.

THE PRIOR ART

U.S. Pat. No. 4,529,438 describes and claims certain herbicidally active aryloxyphenoxy pentanoates and derivatives and discloses methods for their manufacture.

The aryloxyphenoxy pentanoate herbicides can be made in a number of different ways. One method described in the literature comprises initially reacting a substituted pyridine compound with a hydroquinone, followed by completion of subsequent processing steps. This method is described in U.S. Pat. No. 4,216,007. A problem with this medthod is that the initial starting compound, the pyridine compound, is very expensive, and subsequent processing steps dilute the percentage of pyridine moiety ending up in the end product, thus increasing significantly the cost of the final product obtained. Desirably, the pyridine moiety is added at the end of the process in order to maximize the percent yield, and minimize the expense of the substituted pyridine compound.

U.S. Pat. Nos. 4,547,582 and 4,540,804 also disclose processes for making various benzyloxyphenoxy pentanoate compounds which are used as intermediates in the production of the aryloxyphenoxy pentanoates referred to above.

New processes are constantly being sought for the preparation of the aforementioned benzyloxyphenoxy pentanoate intermediates, other benzyloxyphenoxy pentanoate compounds and the aryloxyphenoxy pentanoate herbicides which can be produced therefrom which require fewer steps, less expensive reagents and higher yielding reactions than has previously been the case.

DESCRIPTION OF THE INVENTION

A new process for the production of certain benzyloxyphenoxy pentanoates has been discovered. The process comprises the steps of:

(a) reacting a benzyloxyphenol of the formula

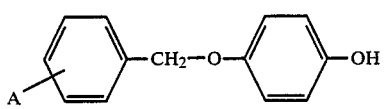

wherein A is selected from the group consisting of hydrogen, lower alkyl having from 1 to 5 carbon atoms, or halogen, with a 3-halo-2-butanone of the formula

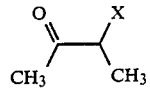

wherein X is selected from the group consisting of chlorine, iodine or bromine, in the presence of a base selected from carbonate salts of alkaline earth or alkali metals, a catalyst selected from the group consisting of alkali metal salts of iodine or bromine, preferably potassium iodide or sodium iodide, and a ketonic solvent preferably selected from the group consisting of methyl ethyl ketone, methyl isobutyl ketone or acetone, to produce a 3-(4-benzyloxyphenoxy)-2-butanone of the formula

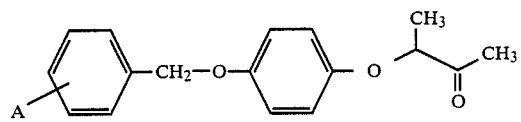

wherein A is as previously defined; and (b) reacting said 3-(4-benzyloxyphenoxy)-2-butanone with a dialkyl carbonate of the formula $(RO)_2CO$, wherein R is an alkyl group having from 1 to 4 carbon atoms in the presence of a base selected from an alkali or alkaline earth metal alkoxide an alkali or alkaline earth metal or their hydrides, and an organic solvent to form 4-(4-benzyloxyphenoxy)-3-oxopentanoate.

The 3-(4-benzoylozyphenoxy)-2-butanone produced by the reaction in step (a) above is a new and novel compound.

This process can be represented schematically as set forth below.

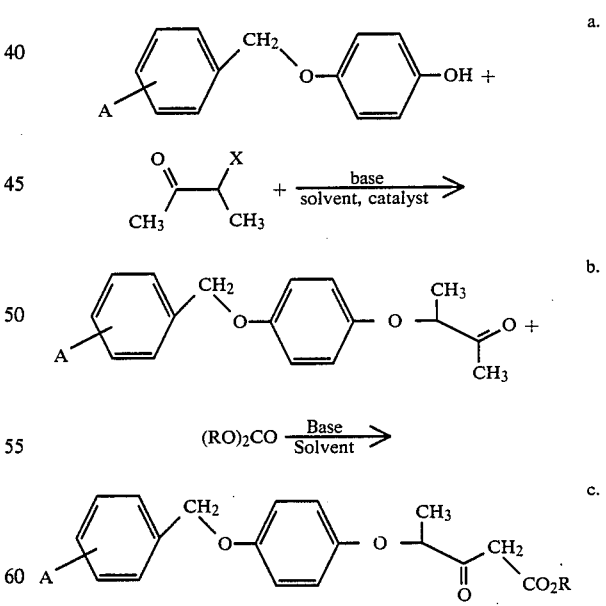

The compounds produced in accordance with the method of this invention, alkyl 4-(4-benzyloxyphenoxy)-3-oxopentanoates, can be used as intermediates in the production of the aforementioned aryloxyphenoxy pentanoates such as are described in U.S. Pat. No. 4,529,438.

The method whereby the alkyl 4-(4-benzyloxyphenoxy)-3-oxopentanoates are converted into the aforementioned aryloxyphenoxy pentanoates is described in U.S. Pat. No. 4,540,804, cols. 5 and 6. In general, the method comprises conversion of the alkyl 4-(4-benzyloxyphenoxy)-3-oxopentanoates, to an alkyl 4-(4-benzyloxyphenoxy)-3-hydroxypentanoate, conversion of this compound to a 3-hydroxy-[4-(3-hydroxyphenoxy)]-pentanoate and in turn reacting the pentanoate compound with various substituted pyridine or phenyl compounds to produce the end product.

In the practice of the process of the invention, the preferred starting compound is 4-benzyloxyphenol, but substituted benzyloxyphenols can also be used. Preferred substituent groups are lower alkyl or halogen moieties. Practically any non-reacting substituent group can be placed on the benzyl moiety, because the entire benzyl moiety is eliminated in subsequent processing steps.

This invention will be more clearly understood by reference to the following examples, which are intended to be illustrative of the process, but not limiting thereof.

EXAMPLE 1

Preparation of 3-(4-Benzyloxyphenoxy)-2-butanone

Into a 50 milliliter (ml), three-necked, round-bottom flask fitted with a thermometer, addition funnel, magnetic stirrer, condenser and nitrogen purge, was charged 4.0 grams (g) of 4-benzyloxyphenol, 0.2 g of potassium iodide, 5.0 g of potassium carbonate and 25 ml of methyl ethyl ketone. The mixture in the flask was stirred at room temperature, and while being stirred was simultaneously charged with 2.13 g of 3-chloro-2-butanone dissolved in 2.5 ml of methyl ethyl ketone, over a 5 minute period.

The reaction mixture was then heated to the reflux temperature. The reaction was allowed to proceed for approximately 3.0 hours. At the end of this time, 0.53 g of potassium carbonate was added to the solution. The reaction was continued for an additional 2 hours, then stopped and the mixture let cool. The reaction mixture was filtered through a glass-fritted funnel to remove the solids, then the liquid portion was stripped. The residue was then rediluted with 30 ml of ether, washed once with 25 ml of 5% sodium hydroxide and once with 25 ml of water. The solution was then dried over magnesium sulfate, filtered, and stripped, yielding 4.85 g (94.5%) of a crude white solid product. Assay analysis by suitable analytical techniques indicated that the product was 4-(4-benzoyloxyphenoxy)-2-butanone.

The process as indicated in Example 1 was repeated a number of times, utilizing molar quantities each of 4-benzyloxyphenol and 3-chloro-2-butanone, and varying quantities of base, catalyst and solvent, as well as differing times and temperatures.

The variou process runs are illustrated in Table 1 below.

TABLE 1

Preparation of 3-(4-Benzyloxyphenoxy)-2-butanone

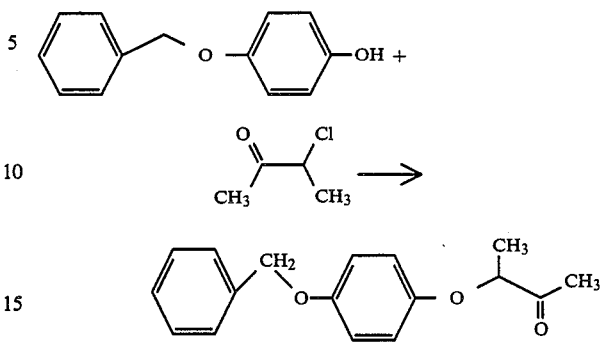

| Mole % $K_2CO_3$ | Catalyst (Mole %) | Solvent | Temp (°C.)/ Time (hrs) | Tech. Yield | Purity (wt. %) |
|---|---|---|---|---|---|
| 200 | KI(6) | MEK* | 80/5 | 94.5 | 97.0 |
| 200 | KI(6) | MIBK** | 115/6 | 91.1 | 94.8 |
| 200 | KI(1) | MEK | 80/4 | 100 | 98.4 |
| 200 | KBr(1) | MEK | 80/6 | 94.1 | 97.5 |
| 200 | — | MEK | 80/7.5 | 92.2 | 93.8 |
| 200 | (1) | MEK | 80/5 | 96.8 | 96.9 |
| 200 | $Cs_2CO_3$(2.5) | MEK | 80/4 | 77.4 | 99.1 |
| — | $Cs_2CO_3$(200) | MEK | 80/6.5 | 97.3 | 90.2 |
| 200$^a$ | KI(1) | MEK | 80/8 | 92.2 | 96.4 |
| 200$^a$ | KI(1) | MIBK | 115/5 | 99.3 | 95.5 |
| 200$^a$ | KI(1) | MIBK | 115/5 | 96.2 | 97.2 |

$^a$ = undried $K_2CO_3$
\* = methyl ethyl ketone
\*\* = methyl isobutyl ketone

Example 2 below is a scale up of the process described in Example I and Table I above, using substantially larger quantities of reactants.

EXAMPLE 2

Preparation of 3-(4-Benzyloxyphenoxy)-2-butanone

Into a 12 liter (l), four-necked, round-bottom flask, fitted with a thermometer, reflux condenser, mechanical stirrer, heating mantle, catch basin and nitrogen purge was charged 740.9 g of 4-benzyloxyphenol, 415.0 g of 3-chloro-2-butanone, 1.023 kilograms (kg) of potassium carbonate, 6.15 g of potassium iodide and 3.7 L of methyl isobutyl ketone. The reaction mixture was heated to 106° C. and the reaction was allowed to proceed for approximately 3 hours and 40 minutes. At that time, an additional charge of 102.28 g of potassium carbonate and 19.25 g of 3-chloro-2-butanone was added and the reaction allowed to proceed another two hours. At that time the reaction was stopped, the reaction mixture was cooled to room temperature, and was allowed to sit overnight. The next day the reaction mixture was reheated to 106° C. It was then allowed to react for an additional 6 hours, for a total of approximately 11 hours reaction time. At that time, the reaction mixture (solution) was cooled to 85° C. and 2.5 liters of warm tap water at 55° C. was added, and the solution stirred for 10 minutes. The water layer was removed, and the remaining organic layer was washed 5 times with 3.5 liters of 5% sodium hydroxide solution and once with 4.0 liters hot tap water. The organic phase was dried over magnesium sulfate, filtered, then stripped, yielding a beige solid which was dried in a vacuum oven overnight at 50° C. The crude yield was 961.85 g of 3-(4-benzyloxyphenoxy)-2-butanone.

EXAMPLE 3

Preparation of Methyl 4-(4-Benzyloxyphenoxy)-3-oxopentanoate 3-(4-Benzyloxyphenoxy)-2-butanone (5.0 g) was dissolved in 25 ml of dimethyl carbonate and added to a 50 ml, three-necked, round-bottom flask fitted with a thermometer, condenser, magnetic stirrer and nitrogen sweep. The solution was heated to 85° C. in an oil bath, then charged with 0.51 g of sodium over a period of 0.5 hour. The resulting clear yellow solution began off-passing after 15 minutes, and then turned a cloudy yellow. After 1 hour, the condenser was replaced with a Vigreux column and distillation head, and the bath temperature was raised to 130° C. Methanol was distilled off for 45 minutes. After approximately 4.5 hours, the reaction was stopped and the solution let cool to room temperature. The dimethyl carbonate was stripped off, and the residue rediluted with 50 ml of ethyl acetate. The solution was then washed with a solution of 50 ml of ice water and 5 ml of acetic acid and then with 50 ml of water. The organic phase was dried over magnesium sulfate, filtered, and stripped. The crude yield was 6.06 g of an orange oil. This was submitted for analysis and found to contain 82% of the desired product, methyl 4-(4-benzyloxyphenoxy)-3-oxopentanoate.

EXAMPLE 4

Preparation of Methyl 4-(4-Benzyloxyphenoxy)-3-oxopentanoate

A 100 ml, three-necked round-bottom flask fitted with a thermometer, magnetic stirrer, addition funnel and nitrogen purge was charged with 0.90 g of sodium hydride, 3.1 ml of dimethyl carbonate and 40 ml of toluene. The solution was heated to between 80° and 85° C., then charged with 5.0 g of 3-(4-benzyloxyphenoxy)-2-butanone dissolved in 10 ml of hot toluene. The reaction mixture was heated to reflux for a period of 2.5 hours. It was then let cool to room temperature and acetic acid was added to neutralize the solution. Thereafter, 25 ml of water was added and the solution then acidified to a pH of 5. The solution was extracted twice with 50 ml of toluene. The toluene layers were washed with 50 ml of water and subsequently dried over magnesium sulfate. The solution was then stripped, yielding 5.47 g of a dark brown oil, identified as the subject compound.

EXAMPLE 5

Preparation of Methyl 4-(4-Benzyloxyphenoxy)-3-oxopentanoate

Into a 25 ml, three-necked round-bottom flask fitted with a thermometer, vigreux column, distillation head, magnetic stirrer, syringe pump and nitrogen sweep was charged 5.0 g of 3-(4-benzyloxyphenoxy)-2-butanone and 10 g of dimethyl carbonate, and the solution heated to 90° C. Thereafter, 2.0 ml sodium methoxide in methanol was added over a period of 50 minutes via a syringe pump. At the end of this addition, the reaction mixture was of a thick, cloudy orange consistency. It was then stirred for 40 minutes and charged with another 2.7 ml of sodium methoxide in methanol over a period of 30 minutes while distilling over methanol. At the end of the addition, the solution was very thick, and another 5 ml of dimethylcarbonate was added to improve the stirring capabilities. The solution was then removed from the heat, cooled to room temperature, and allowed to set for one hour. After this time, it was reheated to reflux temperature, and another 1.1 ml of sodium methoxide in methanol was charged over a period of 13 minutes. Fifteen minutes after the addition, the heat was removed, and the solution cooled to room temperature. The solution was then stripped to remove dimethyl carbonate and then mixed with 50 ml of ethyl acetate, 50 ml of ice water and 5 ml of acetic acid. The resulting mixture was shaken and separated and the organic phase was washed with 50 ml of water, and dried over magnesium sulfate. The solution was then filtered and stripped on an aspirator, yielding 5.75 g of a dark brown oil which was identified as being the subject compound by suitable analysis.

4-Benzyloxyphenol, the preferred starting compound for step (a) in the process of the invention, is commercially available, as are various substituted 4-benzyloxy phenols.

The preferred butanone compound for use in step (a) is 3-chloro-2-butanone. This compound is commercially available. Other halogen substituents such as bromine or iodine can be used instead of chlorine, with good success.

The base used in step (a) of the process of the invention is preferably potassium carbonate. However, any other base can be used which is strong enough to pull off the proton on the phenol compound. Thus, other bases which can be used include, for example, cesium carbonate and other alkaline earth or alkali metal carbonates.

In order for the reaction of step (a) to proceed adequately, a catalyst may be used. Suitable catalysts include potassium iodide or sodium iodide. The preferred catalyst is potassium iodide.

The solvent used in step (a) in the process of the invention is preferably methyl isobutyl ketone. However, other solvents such as methyl ethyl ketone, acetone, or any other ketonic solvent, would also be suitable.

The solvents, catalysts and bases are all commercially available.

The preferred reactant to be reacted with the benzyloxyphenoxy butanone in step (b) of the process of the invention is dimethylcarbonate. This is because the preferred end product is the methyl ester of the pentanoic acid. If an ester other than the methyl ester is desired, then the reactant should have an alkyl group which is the same as the desired ester group, as, for example, diethylcarbonate, to form the ethyl ester, or dipropyl carbonate to form the propyl ester.

In step (b) of the process of the invention, the base is one which can be an alkali or alkaline earth metal alkoxides, the alkali metal or alkaline earth metal itself or their metal hydrides. Preferred bases include sodium hydride, sodium methoxide and metallic sodium. The alcohol derivative should be one which has an alkyl group corresponding to that of the ester on the end product.

Step (b) also requires an organic solvent. Suitable solvents include methyl ethyl ketone, excess dimethyl carbonate, toluene, dimethylsulfoxide and the like.

Step (a) in the process of the invention is preferably conducted at reflux temperature, which will vary depending on the reactants utilized. Step (b) is conducted at a temperature which will vary, depending on the reactants and solvent used, but in general will range from about 50° to about 140° C. The reaction takes a number of hours to complete. This will vary depending on the reaction temperature and specific catalyst used.

The reaction is preferably conducted at atmospheric pressure at all times.

The preferred ratio of butanone to phenol used in step (a) of the process of the invention is approximately equimolar, while the preferred mole ratio of iodide or bromide salts to phenol is approximately 1:100.

In step (b), sufficient base must be used to react effectively with the butanone produced in step (a). In general, a mole ratio of 1:1 can be used.

It will be recognized by those skilled in the art that variations in molar ratios, times, temperatures and solvents used in the various steps in the process of the invention can be made without departing from the spirit and scope of the claims as appended.

What is claimed is:

1. A method for the preparation of benzyloxyphenoxy pentanoates which comprises the steps of:
   (a) reacting a benzyloxyphenol of the formula

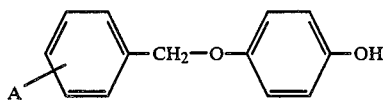

wherein A is selected from the group consisting of hydrogen, lower alkyl having from 1 to 5 carbon atoms, or halogen, with a 3-halo-2-butanone of the formula

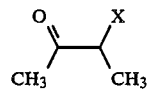

wherein X is selected from the group consisting of chlorine, iodine or bromine, in the presence of a base selected from carbonate salts of alkaline earth or alkali metals, a catalyst selected from the group consisting of alkali metal salts of iodine or bromine, preferably potassium iodide or sodium iodide, and a ketonic solvent preferably selected from the group consisting of methyl ethyl ketone, methyl isobutyl ketone or acetone, to produce a 3-(4-benzyloxyphenoxy)-2-butanone of the formula

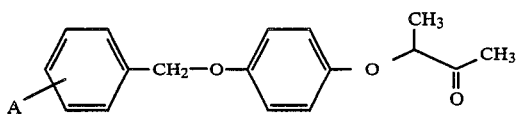

wherein A is as previously defined; and
   (b) reacting said 3-(4-benzyloxyphenoxy)-2-butanone with a dialkyl carbonate of the formula (RO)$_2$CO, wherein R is an alkyl group having from 1 to 4 carbon atoms in the presence of a base selected from an alkali or alkaline earth metal alkoxide or an alkali or alkaline earth metal or their hydrides, and an organic solvent to form 4-(4-benzyloxyphenoxy)-3-oxopentanoate.

2. The method of claim 1 wherein the base used in step (a) is potassium carbonate and in step (b) is sodium methoxide.

3. The method of claim 1 wherein said 3-halo-2-butanone is 3-chloro-2-butanone.

4. The method of claim 1 wherein said benzyloxyphenol is 4-benzoyloxyphenol.

5. The method of claim 1 wherein said solvent used in step (a) is methyl isobutyl ketone and in step (b) is excess dimethyl carbonate.

6. The method of claim 1 wherein the catalyst of step (a) is potassium iodide.

7. The method of claim 1 wherein the solvent used in step (a) is methyl ethyl ketone.

8. The method of claim 1 wherein the dialkyl carbonate in step (b) is dimethyl carbonate.

9. The method of claim 1 wherein the reaction of step (a) is conducted at reflux temperature.

10. The method of claim 1 wherein said ketonic solvent is selected from the group consisting of methyl ethyl ketone, methyl isobutyl ketone and acetone.

* * * * *